(12) United States Patent
Orjuela et al.

(10) Patent No.: US 8,293,935 B2
(45) Date of Patent: Oct. 23, 2012

(54) CARBOXYLIC ACID RECOVERY AND METHODS RELATED THERETO

(75) Inventors: Alvaro Orjuela, Bogata (CO); Abraham Yanez-McKay, Okemos, MI (US); Carl Lira, East Lansing, MI (US); Dennis Miller, Okemos, MI (US)

(73) Assignee: Board of trustees of Michigan State University, East Lansing, MI (US)

( * ) Notice: Subject to any disclaimer, the term of this patent is extended or adjusted under 35 U.S.C. 154(b) by 0 days.

(21) Appl. No.: 13/145,731

(22) PCT Filed: Dec. 2, 2010

(86) PCT No.: PCT/US2010/058787
§ 371 (c)(1),
(2), (4) Date: Jul. 21, 2011

(87) PCT Pub. No.: WO2011/069008
PCT Pub. Date: Jun. 9, 2011

(65) Prior Publication Data
US 2011/0275851 A1 Nov. 10, 2011

Related U.S. Application Data

(60) Provisional application No. 61/265,851, filed on Dec. 2, 2009.

(51) Int. Cl.
*C07C 69/66* (2006.01)
*C07C 69/40* (2006.01)
*C07C 69/34* (2006.01)
(52) U.S. Cl. .......... 560/179; 560/190; 560/191
(58) Field of Classification Search .......... None
See application file for complete search history.

(56) References Cited

U.S. PATENT DOCUMENTS

| 5,034,105 | A | 7/1991 | Berglund et al. |
| 5,143,833 | A | 9/1992 | Datta |
| 5,143,834 | A | 9/1992 | Glassner et al. |
| 5,168,055 | A | 12/1992 | Datta et al. |
| 5,831,122 | A | 11/1998 | Eyal |
| 5,958,744 | A | 9/1999 | Berglund et al. |
| 6,265,190 | B1 | 7/2001 | Yedur et al. |
| 6,274,744 | B1 * | 8/2001 | Burst et al. ............ 549/315 |
| 6,641,734 | B2 | 11/2003 | Cockrem et al. |
| 6,777,213 | B2 | 8/2004 | Staley |
| 6,803,217 | B2 | 10/2004 | Moore et al. |
| 6,902,917 | B1 | 6/2005 | Moore et al. |
| 2006/0014977 | A1 * | 1/2006 | Miller et al. ............ 560/179 |
| 2006/0252956 | A1 | 11/2006 | Miller et al. |
| 2007/0129565 | A1 | 6/2007 | Sutton et al. |

FOREIGN PATENT DOCUMENTS

| CA | 2625511 A1 | 9/2009 |
| WO | WO-9300440 | 1/1993 |
| WO | WO-2011069008 A1 | 6/2011 |

OTHER PUBLICATIONS

"International Application Serial No. PCT/US2010/058787 Search Report mailed Apr. 6, 2011", 6 pgs.
"International Application Serial No. PCT/US2010/058787 Written Opinion mailed Apr. 6, 2011", 7 pgs.
Gould, Philip L, "Salt selection for basic drugs", International Journal of Pharmaceutics, 33(1-3), (Nov. 1986), 201-217.
Luque, R, et al., "Chemical transformations of succinic acid recovered from fermentation broths by a novel direct vacuum distillation-crystallisation method", Green Chemistry, vol. 11, XP008134856, ISSN: 1463-9262, (Nov. 19, 2008), 193-200.

* cited by examiner

*Primary Examiner* — Paul A Zucker
(74) *Attorney, Agent, or Firm* — Clark IP Law, PLC

(57) ABSTRACT

A method of producing an alkyl ester of a carboxylic acid is provided, the method comprising: adding an alkanol and a mineral acid to a carboxylic acid salt to provide a carboxylic acid/alkanol solution and a precipitated mineral acid salt; separating the mineral acid salt from the carboxylic acid/alkanol solution; esterifying the carboxylic acid; and isolating an alkyl ester of the carboxylic acid.

22 Claims, 7 Drawing Sheets

KEY FOR 6A AND 6B
(+) - SA, (□) - MES, (▲) - DES, (X) - AcAc, (●) - EtAc, (○) - Total

KEY FOR 7A AND 7B:

(+) – SA, (□) – MES, (▲) – DES, (○) – Total succinate

CARBOXYLIC ACID RECOVERY AND METHODS RELATED THERETO

RELATED APPLICATIONS

This application is a U.S. National Stage Filing under 35 U.S.C. 371 from International Application No. PCT/US2010/058787, filed Dec. 2, 2010, and published in English as WO 2011/069008 on Jun. 9, 2011, which claims the benefit under 35 U.S.C. 119(e) of U.S. Provisional Application Ser. No. 61/265,851 filed on Dec. 2, 2009, entitled, "Carboxylic Acid Recovery From Fermentation Solutions," which applications and publications are hereby incorporated by reference in their entireties.

BACKGROUND

Succinic acid is a dicarboxylic acid that can be produced by fermentation. Carboxylic acids are typically obtained from the aqueous fermentation solution as the corresponding carboxylic acid salts. Such salts typically include sodium or calcium as the cation. However, other acid co-products, such as acetic acid and formic acid, are also found as salts in the same aqueous solution, thereby increasing the expense of deriving value from the fermentation process.

SUMMARY

The inventors recognize a need for providing an inexpensive process to extract and purify carboxylic acids, such as succinic acid, from fermentation broths, and to esterify such carboxylic acids to their alkyl esters. The methods described herein are suitable for carrying out the processes on a large scale.

Accordingly, in one embodiment, a method of producing an alkyl ester of a carboxylic acid comprising adding an alkanol (such as $C_1$-$C_8$)alkanol and a mineral acid to a carboxylic acid salt to provide a carboxylic acid/alkanol solution and a precipitated mineral acid salt; separating the mineral acid salt from the carboxylic acid/alkanol solution; esterifying the carboxylic acid; and isolating an alkyl ester of the carboxylic acid is provided. In one embodiment, the method further comprises adding additional alkanol to the reactive distillation column; removing an alkanol-water azeotrope from the reactive distillation column, wherein the carboxylic acid salt is in an aqueous solution, and, prior to the adding step of claim 1, removing water from the aqueous solution to provide a carboxylic acid salt and water mixture containing less than about 15 wt % water.

The carboxylic acid can include, but is not limited to, a mono-carboxylic acid, a dicarboxylic acid, a tricarboxylic acid, a tetracarboxylic acid, and/or similar carboxylic acid containing compounds. As such, the term carboxylic acid refers to a carboxylic acid containing compounds that includes one or more carboxylic acid moieties, and an alkyl ester of a carboxylic acid or a carboxylic acid ester refers to the corresponding ester of such carboxylic acids. The methods described herein provide for the alkylation of such carboxylic acids, and for the isolation of any one or more of the individual corresponding alkyl esters. Therefore, the recitation of dicarboxylic acid, where noted herein, is an example according to various embodiments. In other embodiments, the terms 'dicarboxylic acid' and 'dialkyl ester' can be replaced with terms such as monocarboxylic acid and monoalkyl ester, tricarboxylic acid, trialkyl ester, tetraalkyl ester, and the like, as would be understood by one of skill in the art.

In one embodiment, a method of preparing a dialkyl ester of a carboxylic acid comprising adding a ($C_1$-$C_8$)alkanol and a mineral acid to a carboxylic acid salt, to provide a carboxylic acid ($C_1$-$C_8$)alkanol solution and a precipitated mineral acid salt; separating the mineral acid salt from the carboxylic acid ($C_1$-$C_8$)alkanol solution; heating the carboxylic acid ($C_1$-$C_8$)alkanol solution in a reactive distillation column to esterify the carboxylic acid; and isolating a dialkyl ester of the carboxylic acid from the reactive distillation column is provided.

In various embodiments, the carboxylic acid salt can be an alkali metal salt, an alkaline earth metal salt, or a combination thereof. The carboxylic acid can include, but is not limited to, succinic acid, malonic acid, maleic acid, malic acid, oxalic acid, itaconic acid, fumaric acid, 2,5-furan dicarboxylic acid, aspartic acid, glucaric acid, glutamic acid, adipic acid, pimelic acid, suberic acid, azeleic acid, sebacic acid, phthalic acid, isophthalic acid, terephthalic acid, acetic acid, formic acid, lactic acid, acrylic acid, citric acid, 3-hydroxypropanoic acid, levulinic acid, propionic acid, butyric acid, isobutyric acid, pyruvic acid, 3- or 4-hydroxybutyric acid, or a combination thereof. Other carboxylic acids, such as other monocarboxylic acids, dicarboxylic acids, or tricarboxylic acids, as well as tetracarboxylic acids, can be esterified using the methods described herein.

The ($C_1$-$C_8$)alkanol can be methanol, ethanol, propanol, butanol, pentanol, hexanol, heptanol, octanol, or a branched isomer of propanol, butanol, pentanol, hexanol, heptanol, or octanol. The mineral acid can be sulfuric acid and the precipitated mineral acid salt is therefore a sulfate salt. Other mineral acids can be used, so long as they are sufficiently insoluble in the ($C_1$-$C_8$)alkanol used in the method. Examples of such mineral acids include, but are not limited to, hydrochloric acid, nitric acid, phosphoric acid, boric acid, hydrofluoric acid, or hydrobromic acid. The precipitated mineral acid salt may therefore be the salt of any of the aforementioned acids, such as an alkali metal salt or alkaline earth metal salt. The precipitated salts can also be hydrated salts, according to various embodiments.

Additional ($C_1$-$C_8$)alkanol can be added to the reactive distillation column, for example, to drive the equilibrium of the esterification reaction toward formation of the esters. Additionally, a ($C_1$-$C_8$)alkanol-water azeotrope can be removed from the reactive distillation column to further drive the reaction.

In some embodiments, the carboxylic acid salt is in an aqueous solution. In such embodiments, water can optionally be removed from the solution to provide a carboxylic acid salt and water mixture. The water content of the mixture can be, for example, less than about 50 wt %, less than about 25 wt %, less than about 15 wt %, less than about 10 wt %, less than about 5 wt %, less than about 3 wt %, less than about 2 wt %, or less than about 1 wt %, of the mixture, prior to the addition of the ($C_1$-$C_8$)alkanol and the mineral acid. In some embodiments, the carboxylic acid salt can be in a substantially dry state, with water present in only salt hydrate forms.

The carboxylic acid salt can be a sodium salt. An alkaline earth metal hydroxide (e.g., calcium hydroxide or magnesium hydroxide) can be added to the aqueous solution to exchange sodium cations of the carboxylic acid salt with alkaline earth metal cations, for example, calcium ions.

The aqueous solution of the carboxylic acid salt can be part of an aqueous fermentation broth, for example, that includes that includes water, various bacteria that can produce carboxylic acids, and nutrients, as well as various carboxylic acids produced by the bacteria, for example, in the form of their corresponding salts. Such methods can also include removing organic solids, such as proteins, lipids, carbohydrates, and bacterial cell components and/or products, from the aqueous fermentation broth by filtration, decantation, centrifugation, or a combination thereof, to provide a separated fermentation broth that includes carboxylic acids, such as dicarboxylic acid, as salts in the aqueous solution. Additional organic compounds other than the carboxylic acid salt can be removed from the fermentation broth, for example, by treatment of the aqueous fermentation broth or the separated fermentation broth with an adsorption or filtration agent, such as activated carbon, molecular sieves, zeolites, and/or diatomaceous earth, and the like.

In one embodiment, the carboxylic acid salt can include sodium succinate, the carboxylic acid can include succinic acid, the mineral acid can include sulfuric acid, and/or the dialkyl ester of the carboxylic acid can include diethyl succinate.

Embodiments of the invention further provide a method of isolating a carboxylic acid from a fermentation broth comprising removing organic solids from an aqueous fermentation broth that includes water, bacteria, nutrients, and a carboxylic acid sodium salt, by filtration, decantation, centrifugation, or a combination thereof, to provide a separated fermentation broth that comprises the carboxylic acid sodium salt; optionally removing organic compounds other than the carboxylic acid sodium salt from the fermentation broth by treatment of the aqueous fermentation broth or the separated fermentation broth with activated carbon; optionally adding an alkaline earth metal hydroxide to exchange sodium cations of the carboxylic acid sodium salt with alkaline earth metal cations; removing water from the separated fermentation broth to precipitate the carboxylic acid sodium salt or a carboxylic acid alkaline earth metal salt, to provide a carboxylic acid salt broth precipitate; optionally heating the carboxylic acid salt broth precipitate to remove additional water; adding a $(C_1-C_8)$alkanol and a mineral acid to the carboxylic acid salt broth precipitate, to provide a mixture of a $(C_1-C_8)$alkanol solution of a resulting carboxylic acid and precipitated sodium sulfate or alkaline earth metal sulfate; separating the sodium sulfate or alkaline earth metal sulfate from the $(C_1-C_8)$alkanol solution of the carboxylic acid to provide a $(C_1-C_8)$alkanol solution of the carboxylic acid; and optionally concentrating the $(C_1-C_8)$alkanol solution of the carboxylic acid to provide the carboxylic acid in concentrated form.

The methods can also include heating the carboxylic acid $(C_1-C_8)$alkanol solution in a reactive distillation column to esterify the carboxylic acid. A dialkyl ester of the carboxylic acid can be isolated from the reactive distillation column Additional $(C_1-C_8)$alkanol can be added to the reactive distillation column, and/or a $(C_1-C_8)$alkanol-water azeotrope can be removed from the reactive distillation column. Furthermore, other carboxylic acid esters, diesters, and the like, can be isolated from the reactive distillation column by taking advantage of the different boiling point of each compound. In any embodiment, the reactive distillation column can be run at atmospheric pressure, under reduced pressure, or at elevated pressure, for example, to further exploit differences in compound boiling points.

Prior to the addition of the $(C_1-C_8)$alkanol and the mineral acid, water can be removed from the solution to provide a carboxylic acid salt and water mixture wherein water comprises less than, for example, about 15 wt % of the mixture. The carboxylic acid salt can be an alkali metal salt, an alkaline earth metal salt, or a combination thereof. The carboxylic acid can include one or more of succinic acid, malonic acid, maleic acid, malic acid, oxalic acid, itaconic acid, fumaric acid, 2,5-furan dicarboxylic acid, aspartic acid, glucaric acid, glutamic acid, adipic acid, pimelic acid, suberic acid, azeleic acid, sebacic acid, phthalic acid, isophthalic acid, or terephthalic acid, acetic acid, formic acid, lactic acid, acrylic acid, citric acid, 3-hydroxypropanoic acid, levulinic acid, propionic acid, butyric acid, isobutyric acid, pyruvic acid, 3- or 4-hydroxybutyric acid, or their corresponding mono- or di$(C_1-C_8)$alkyl esters, or a combination thereof.

The $(C_1-C_8)$alkanol can include, for example, methanol, ethanol, propanol, butanol, pentanol, hexanol, heptanol, octanol, or a branched isomer of propanol, butanol, pentanol, hexanol, heptanol, or octanol. In some embodiments, the $(C_1-C_8)$alkanol can be one or more of methanol, ethanol, n-propanol, n-butanol, 2-butanol, or tert-butanol. The mineral acid can be, for example, sulfuric acid and the precipitated mineral acid salt can be the corresponding salt of the mineral acid.

The mixture the $(C_1-C_8)$alkanol solution of the carboxylic acid and precipitated sodium sulfate or alkaline earth metal sulfate can be about 23° C. to about the decomposition temperature of the alkanol or the organic diacid in the presence of aqueous sulfuric acid. The $(C_1-C_8)$alkanol can be ethanol and the temperature of the broth after adding the mineral acid can be maintained at about 23° C. to about 78° C.

The ratio of the amount of the carboxylic acid to $(C_1-C_8)$ alkanol, in the mixture of the $(C_1-C_8)$alkanol solution of the carboxylic acid and precipitated sodium sulfate or alkaline earth metal sulfate, can be, for example, about 5 wt % carboxylic acid in alkanol, to about 1 molar equivalent of the carboxylic acid to 2 molar equivalents of alkanol. The ratio of the amount of the carboxylic acid to $(C_1-C_8)$alkanol can also be about 1 molar equivalent of the carboxylic acid to 2 molar equivalents of alkanol, and the corresponding dialkyl ester of the diacid is produced.

When mineral acid salts (e.g., a sodium sulfate or alkaline earth metal sulfate) are separated from the carboxylic acid solution, other components that are insoluble in a $(C_1-C_8)$ alkanol can also be removed. The residual carbohydrates can include, for example, glucose, and the removal can be by precipitation.

The fermentation broth can include, for example, an aqueous solution of a succinate salt, a solid form of a succinate salt, or both. Sodium succinate can be present in the fermentation broth.

The methods can further include esterification of the carboxylic acid in the $(C_1-C_8)$alkanol solution of the carboxylic acid. The carboxylic acid in the $(C_1-C_8)$alkanol solution of the carboxylic acid can be converted to its corresponding $(C_1-C_8)$alkyl diester. The $(C_1-C_8)$alkyl diester can be isolated from other compounds by distillation, thereby providing an isolated and purified $(C_1-C_8)$alkyl diester. The carboxylic acid in the $(C_1-C_8)$alkanol solution of the carboxylic acid can be, for example, succinic acid, and the isolated and purified $(C_1-C_8)$alkyl diester can be diethyl succinate.

Embodiments of the invention further provide for a method for isolating diethyl succinate comprising removing organic solids from an aqueous fermentation broth that includes water, bacteria, nutrients, and sodium succinate, by filtration, decantation, centrifugation, or a combination thereof, to provide a separated fermentation broth that comprises sodium succinate; optionally removing organic compounds other than the sodium succinate from the fermentation broth by treatment of the aqueous fermentation broth or the separated fermentation broth with activated carbon; optionally adding an alkaline earth metal hydroxide to exchange sodium cations of sodium succinate with alkaline earth metal cations; removing water from the separated fermentation broth to precipitate the sodium succinate or alkaline earth metal succinate, to provide a succinate broth precipitate; optionally heating the succinate broth precipitate to remove additional water; adding ethanol and sulfuric acid to the succinate broth precipitate to provide a mixture of an ethanol solution of succinic acid and precipitated sodium sulfate or alkaline earth metal sulfate; separating the sodium sulfate or alkaline earth metal sulfate from the ethanol solution of succinic acid; esterifying the succinic acid in the ethanol solution in a reactive distillation column to provide diethyl succinate; and isolating the diethyl succinate from other compounds in the reactive distillation column to provide isolated and purified diethyl succinate.

One or more of the other compounds in the reactive distillation column can include succinic acid, malonic acid, maleic acid, malic acid, oxalic acid, itaconic acid, fumaric acid, 2,5-furan dicarboxylic, aspartic acid, glucaric acid, glutamic acid, adipic acid, pimelic acid, suberic acid, azeleic acid, sebacic acid, phthalic acid, isophthalic acid, terephthalic acid, acetic acid, formic acid, lactic acid, citric acid, lactic acid, 3-hydroxypropanoic acid, levulinic acid, propionic acid, butyric acid, pyruvic acid, or their corresponding mono- or di($C_1$-$C_8$)alkyl esters, or a combination thereof.

In some embodiments, carboxylic acid can be esterified even before the use of a reactive distillation column Monoesterification can occur in the presence of the mineral acid, as well as various amounts of diesterification, depending on reaction conditions. The methods can include employing a fixed bed reactor for such esterification, prior to employing a reactive distillation column.

Prior to obtaining the separated fermentation broth, the fermentation broth can be neutralized during fermentation to adjust the pH to biogenically acceptable levels. In one embodiment, the pH range is adjusted to about 2.0 to about 10.0, or about 4.0 to about 9.0, or to any 2-3 pH units in a range beginning at 2 and ending at 10.

The methods described herein are efficient, cost effective, and produce less waste than many conventional methods, thereby reducing the overall costs of preparing and isolating carboxylic acids and their corresponding esters. Esters of organic acids are valuable commercial products that can be used as synthetic building blocks for pharmaceuticals, and as ingredients for cosmetic compositions, and industrial solvents and cleaners. Examples of useful synthetic building blocks and solvents include tetrahydrofuran, γ-butyrolactone, 1,4-butane diol, pyrrolidionones, acid anhydrides such as succinic anhydride, and alkylidene alkanates, for example, methylidene succinate.

DETAILED DESCRIPTION

Figure 1:
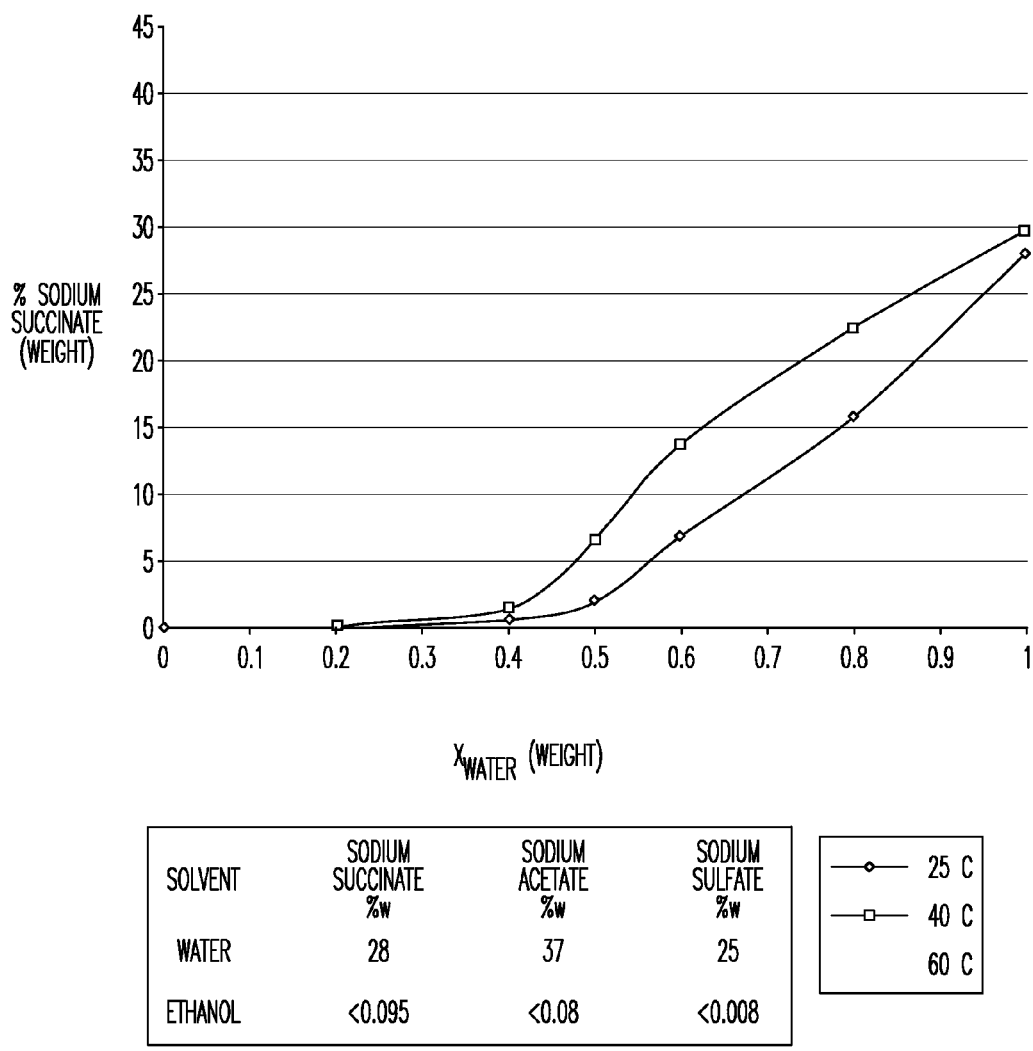
FIG. 1 illustrates the solubility of sodium succinate and sodium acetate in ethanol/water mixtures according to embodiments of the present invention.

In the following detailed description of embodiments of the invention, embodiments are described in sufficient detail to enable those skilled in the art to practice them, and it is to be understood that other embodiments may be utilized and that chemical and procedural changes may be made without departing from the spirit and scope of the present subject matter. The following detailed description is, therefore, not to be taken in a limiting sense, and the scope of embodiments of the present invention is defined only by the appended claims.

The Detailed Description that follows begins with a definition section followed by a brief background discussion, a description of the embodiments, examples and a conclusion.
Definitions As used herein, the term "broth" or "fermentation broth" refer to a reaction mixture wherein a microorganism consumes a biomass substrate, such as a carbohydrate monomer or oligomer, to produce an organic product. The broth typically contains water, one or more microorganisms, nutrients for the microorganism, and the biomass substrate, as well as the desired product once fermentation has begun. Microorganisms known to produce succinic acid by fermentation include, for example, *Anaerobiospirillum succiniciproducens* (e.g., at 50.3 g/L), *Actinobacillus succinogenes* (e.g., at 94-106 g/L), *Mannheimia succiniciproducens* (e.g., at 52.4 g/L), and *Escherichia coli* (e.g., at 99 g/L).

As used herein, the terms "organic diacid" and "dicarboxylic acid" refers to an organic compound that includes two carboxylic acid groups. Typical dicarboxylic acids include ($C_1$-$C_{20}$)alkyl chains that have two carboxylic acid groups on a linear chain. In several embodiments, the organic diacids are alpha-omega diacids, where one carboxylic acid moiety is C1 of the alkyl chain and the second carboxylic acid moiety is the terminal carbon of the alkyl chain. The alkyl chain can be optionally substituted, such as in the case of itaconic acid, aspartic acid, and glucaric acid. Examples include, but are not limited to, malic acid (C3), succinic acid (C4), glutaric acid (C5), and adipic acid (C6).
Background on Carboxylic Acid Recovery Conventional methods of carboxylic acid recovery typically require the production of pure crystalline acids as an intermediate. Such a requirement limits the ability of these methods to achieve high yields on a large scale. Known methods often produce significant amounts of waste products, such as waste solvents. Known methods also have several drawbacks, including deactivation or fouling of required resins and membranes, generation of undesirable side products or contaminants, excessive energy consumption, and expensive reagent requirements.

Methods requiring resins and membranes, such as in an ion exchange step, not only have problems with resin and membrane fouling, but are also expensive, due to the need to regenerate the resins and membranes, typically with inorganic acids. Other processes require the use of inorganic acids to separate a resulting amine-acid adduct, thereby creating additional waste disposal requirements.

Yet other processes using equivalent volumes of organic solvent and aqueous solution of succinic acid cause an increase in material and energy consumption during separation. With such methods, carboxylic acids are also lost in the dilute residual aqueous stream, thereby further decreasing the overall efficiency of such processes.

Discussion of Embodiments

In various embodiments, the methods described herein provide for the recovery of a carboxylic acid as its corresponding ester, and its separation from other acids formed in fermentation. Formation of alkyl esters with higher boiling points than other compounds in a broth permits separation of the desired alkyl ester from other acid esters by relatively simple techniques, such as distillation. In an exemplary embodiment, the recovered acid is a carboxylic acid, such as succinic acid, and the alkyl ester is a dialkyl succinate. Methods of employing reactive distillation column techniques are well known in the art; see for example, Asthana; Kolah; Vu; Lira; and Miller; "A Kinetic Model for Esterification of Lactic Acid and Its Oligomers," *Ind. Eng. Chem. Res.* 45, 5251-5257 (2006), and references cited therein.

A variety of acid and diacid starting materials, specifically carboxylic acids produced by fermentation, can be used in the methods described herein. These carboxylic acids include, but are not limited to, succinic, maleic, oxalic, acetic, formic, lactic, citric, itaconic, 3-hydroxypropanoic, levulinic, fumaric, butyric, propionic, 2,5-furan dicarboxylic, aspartic, glucaric, glutamic, and pyruvic acids, and their mixtures. The methods include esterification of such acids to provide the corresponding dialkyl esters, for example, their diethyl esters. The methods allow for the preparation of a variety of mono-esters, di-esters, and tri-esters, depending on the carboxylic acid present in the culture broth and/or esterification chamber.

In one embodiment, the process includes extraction of a mixture of acids from a concentrated fermentation broth directly into an alcohol, such as ethanol. Such a step allows bypassing conventional purification steps used to remove co-product carboxylic acids, and further alleviates the step of providing pure succinic acid as an intermediate. In one embodiment, succinic acid is extracted from its sodium salt. Extraction of the succinic acid from various other salts, such as those formed with $K^+$, $NH_4^+$, $Ca^{2+}$, and/or $Mg^{2+}$, may also be employed in the methods described herein.

Recovery of carboxylic acids and/or their alkyl esters can include a variety of optional steps. Such steps include, but are not limited to, a fermentation broth separation step (1). Such separation steps can take the form of a filtration step to remove solids (e.g., organic solids such as proteins, macromolecules, and cell membranes) and/or a fermentation broth treatment step, such as an adsorption treatment with activated carbon, to remove soluble proteins and macromolecules.

In many embodiments, an evaporation step (2) is used to evaporate water from the fermentation broth to precipitate and/or dry acid salts, such as carboxylic acid salts, although the invention is not so limited. Depending on the nature of the salt, it may be desirable to leave some water in crystal hydrate form, or it may be desirable to calcine the salt at elevated temperature to break the hydrate, for example, about 120° C. for sodium succinate. In some embodiments, moisture can be left behind on the crystals, depending on the amount of water removed by hydrates of the sulfate salts formed in a subsequent step. In some embodiments, up to about 10 wt % of free water can be allowed to remain in the salt mixture, while still obtaining suitable purification and esterification results. In other embodiments, substantially all free water can be removed. In such instances, only water in a hydrate form will remain, which can be up to about 50% of the mass of the mixture. Sodium sulfate and glucose have low solubility in ethanol so long as less than about 20 wt % of water is present.

In a variation of the process, alkali metal or alkaline earth metal hydroxide, such as calcium hydroxide, can be added to an acid salt (e.g., succinate) solution, such as a sodium succinate solution, to precipitate an acid salt, such as a calcium salt from the carboxylic acid, thereby displacing an alkali metal, such as sodium. The residual solution, e.g., a sodium hydroxide solution, can then be sterilized and recycled to the fermentor for neutralization purposes. The recovered salt, e.g., a calcium salt, can then be treated with an alkanol.

In one embodiment, an acid salt is physically dispersed (3) into an alkanol to form an acid salt/alcohol slurry. The alkanol is necessarily present in an amount sufficient to solubilize the free carboxylic acid at the working temperature. Extraction of the acid can be achieved with ethanol, or various other alcohols such as, but not limited to, methanol, propanol, isopropanol, C4 alcohols, and $(C_1\text{-}C_6)$diols and triols, further including any C1 to C8 alcohol.

A mineral acid, such as sulfuric acid $(H_2SO_4)$, can then be added (4) in a sufficient amount, e.g., a stoichiometric amount, to protonate the salts, thereby forming free carboxylic acids, which are soluble in the alkanol, and sulfate salts which are not soluble in the alkanol. In an exemplary embodiment, an ethanol solution of a mineral acid, for example, $H_2SO_4$, is added to a succinate salt to form a succinate salt/ethanol slurry, with the cation binding tightly with the sulfate and precipitating out.

While the methods described herein can be suitably carried out at room temperature (~23° C.), in one embodiment, higher temperatures, such as the normal boiling point of the alkanol, or higher, are employed to reduce operation time and increase ester production rates. In one embodiment, heat is added to accelerate the reaction of the mineral acid with the carboxylic acid salt and/or the reaction of the resulting free carboxylic acid with the alkanol, e.g., by raising the temperature of the solution to above room temperature, for example, to about 30° C., to about 40° C., to about 50° C., to about 75° C., or to about 100° C., or to the boiling point of the alkanol.

While the solution is optionally heated and cation exchange on the acid salt (e.g., a succinate salt) from sodium/calcium to hydrogen is undergoing completion, excess $H_2SO_4$ can catalyze the esterification of soluble carboxylic acids with the alkanol to form alkyl esters.

In one embodiment, the acid salts, such as the sulfate salts, are separated (5) from the alkanol/carboxylic acid solution, such as with filtration. Any residual solution can be further processed by reactive distillation to complete the esterification of the carboxylic acids to their esters in the alkanol solution to form the acid salt and other acid esters.

The mass ratio of alkanol to salts depends on the solubility of extracted acids at the working temperature. Along with the free acid formation and sulfate salt formation taking place in step 4) above, esterification between carboxylic acids and alcohol occurs, catalyzed by non-reacted $H_2SO_4$. The water produced by esterification can be captured by the sulfate salt because sulfate salts are most stable in their hydrated form.

Formation of the hydrated sulfate salts drives the esterification reaction forward, e.g., toward completion to form ethyl esters, thereby further reducing the solubility of the sulfates, increasing the solubility of carboxylic acids, and improving the separation of the organic compounds.

After filtration to remove sulfate salts (step 5), the liquid solution of alkanol, acids, and esters can be driven to complete esterification in a reactive distillation column. In such reactive distillation columns, a diester, such as dialkyl succinate, is obtained from the bottom of the column.

The alkyl esters of the co-product acids are recovered from the top of the column because of their lower boiling points. For example, one stage to produce diethyl succinate and separate it from other ethyl esters and excess alcohol can be performed in a reactive distillation column, using the method described in U.S. Patent Publication No. 2006/0252956 to Miller, et al., and/or U.S. Pat. No. 5,599,976 (2007) to Sutton, et al., both of which are hereby incorporated by reference in their entirety. Succinic esters can also be readily converted to derivatives such as butanediol, tetrahydro-furan, γ-butyrolactone, and various salts.

In one embodiment, calcium hydroxide is added to a sodium succinate solution to precipitate a calcium salt of the carboxylic acid, thereby displacing sodium. Unlike conventional methods which require neutralization of an aqueous culture broth with calcium hydroxide ($Ca(OH)_2$) to precipitate the calcium salt, in the novel methods described herein, the solids produced are separated and treated with a mineral acid, such as $H_2SO_4$, to release the acid, such as succinic acid, in an aqueous solution, with a sulfate, such as calcium sulfate as a byproduct. In one embodiment, one of the final steps occurs in one or more ion exchange columns, where the acid is retained and then released again by an inorganic acid and concentrated by successive crystallizations, although the invention is not so limited.

In various embodiments, the residual sodium hydroxide solution is sterilized and recycled to the fermentor for neutralization purposes. The salt, such as a calcium salt, is treated with an alcohol, such as an alkanol.

FIG. 1 illustrates solubility measurements of sodium salts in mixtures of ethanol and water. The low solubility of sodium succinate in pure ethanol is remarkable compared with its solubility in water. Even at 20% by mass of water in ethanol, the solubility of sodium succinate is very low, indicating that azeotropic ethanol could be used during acidification. Solubilities in pure ethanol were determined by inductively coupled plasma mass spectrometry (ICP-MS) because of the low salt concentrations achievable. Solubilities in ethanol-water mixtures were obtained gravimetrically.

Carboxylic Acid Recovery from Fermentation Solutions: Process Description

When succinic acid and other organic acids are produced in fermentation, they must be neutralized to maintain the pH around 7 so that the organisms of the fermentation broth can continue to function. The acids are thus converted to salts as the fermentation reaches completion. The fermentation broth containing the salts is centrifuged to remove cells and then treated with activated carbon to remove protein fragments and colorizing agents. When these steps are completed, the acid salt solution can be concentrated by removing the majority of water. The acid salts are then treated to recover the organic acid in partially esterified form. The partially esterified organic acids can then be further converted entirely to the corresponding esters by reaction in a reactive distillation column.

Sodium or calcium succinate reacts with sulfuric acid in alkanol solvents, such as ethanol. Succinate salts are not soluble in alcohol, but succinic acid produced by the acidification is soluble in ethanol to approximately 8% w/w at room temperature.

In one embodiment, the acidification reactions are as follows:

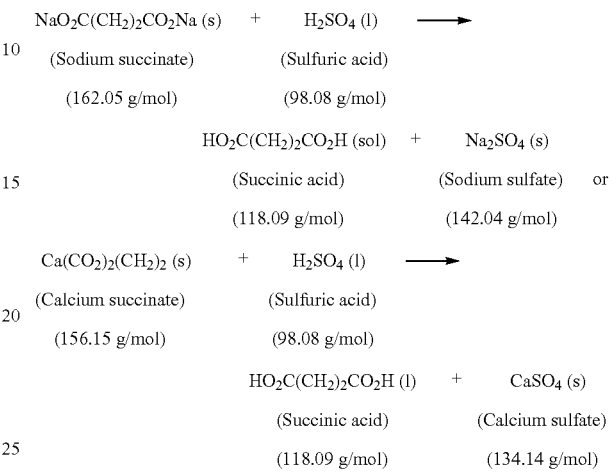

When ethanol or another alkanol is used as the solvent, sulfuric acid can also acts as an esterification catalyst. In such instances, succinic acid is then converted into, e.g., monoethyl succinate and diethyl succinate. These reactions are equilibrium limited, with equilibrium constants of around 4.2 and 1.2, respectively. Representative equilibrium equations are as follows:

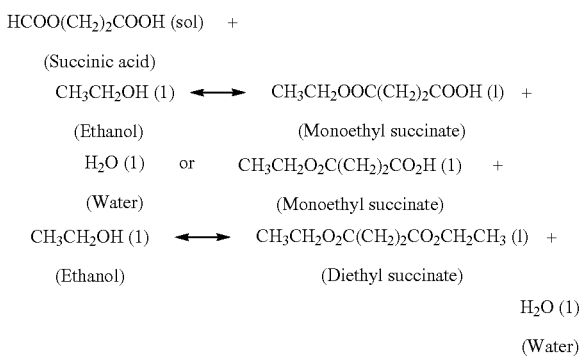

A portion of the water produced by the equilibrium reaction can be adsorbed by solid sulfates, driving the esterification reaction toward the products:

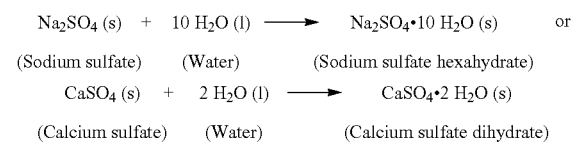

Intermediate products may be produced during the process, such as the esters of monobasic sodium salt or terminal esters in the polymeric structure of calcium succinate.

$NaO_2C(CH_2)_2CO_2H$ (sol) +

(Monosodium succinate)

$CH_3CH_2OH$ (l) ⇌ $NaO_2C(CH_2)_2CO_2CH_2CH_3$ (sol) +

(Ethanol)            (Sodium-ethylsuccinate)

$H_2O$ (l)

(Water)

An equilibrium reaction to produce sodium bisulfate can also occur:

$Na_2SO_4$ (s) +

(Sodium sulfate)

$H_2SO_4$ (l) ⇌ $NaHSO_4$ (s) + $H_2O$ (l)

(Sulfuric acid)   (Sodium Bisulfate)  (Water)

Each of these reactions can occur sequentially or simultaneously during the acidification process, depending on the temperature, $H_2SO_4$ excess, and duration of the reactions.

Figure 2:
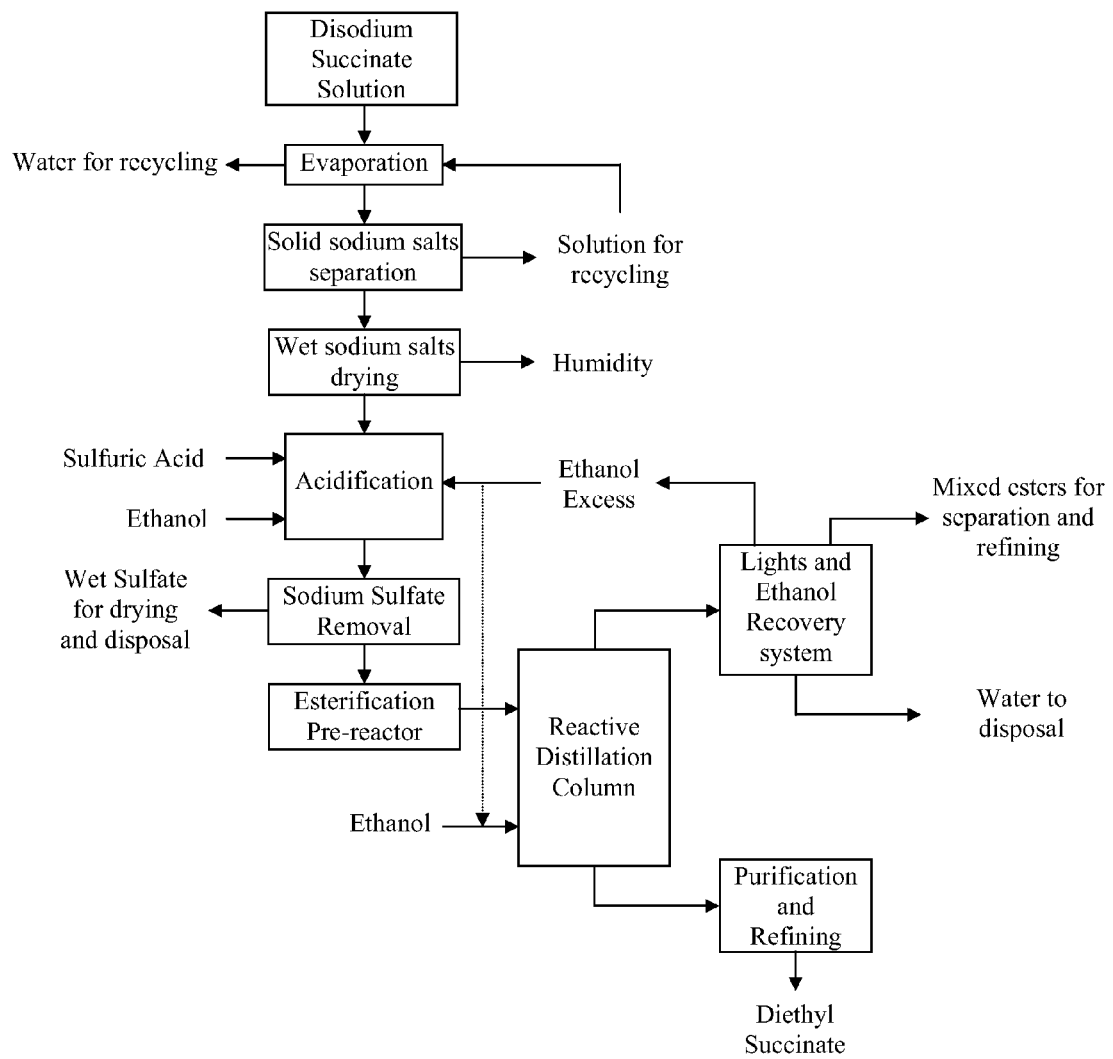
FIG. 2 illustrates a process flow diagram for succinic acid recovery from an aqueous solution, and its conversion to diethyl succinate using a reactive distillation process, including an intermediate evaporation method, according to embodiments of the invention.
Figure 3:
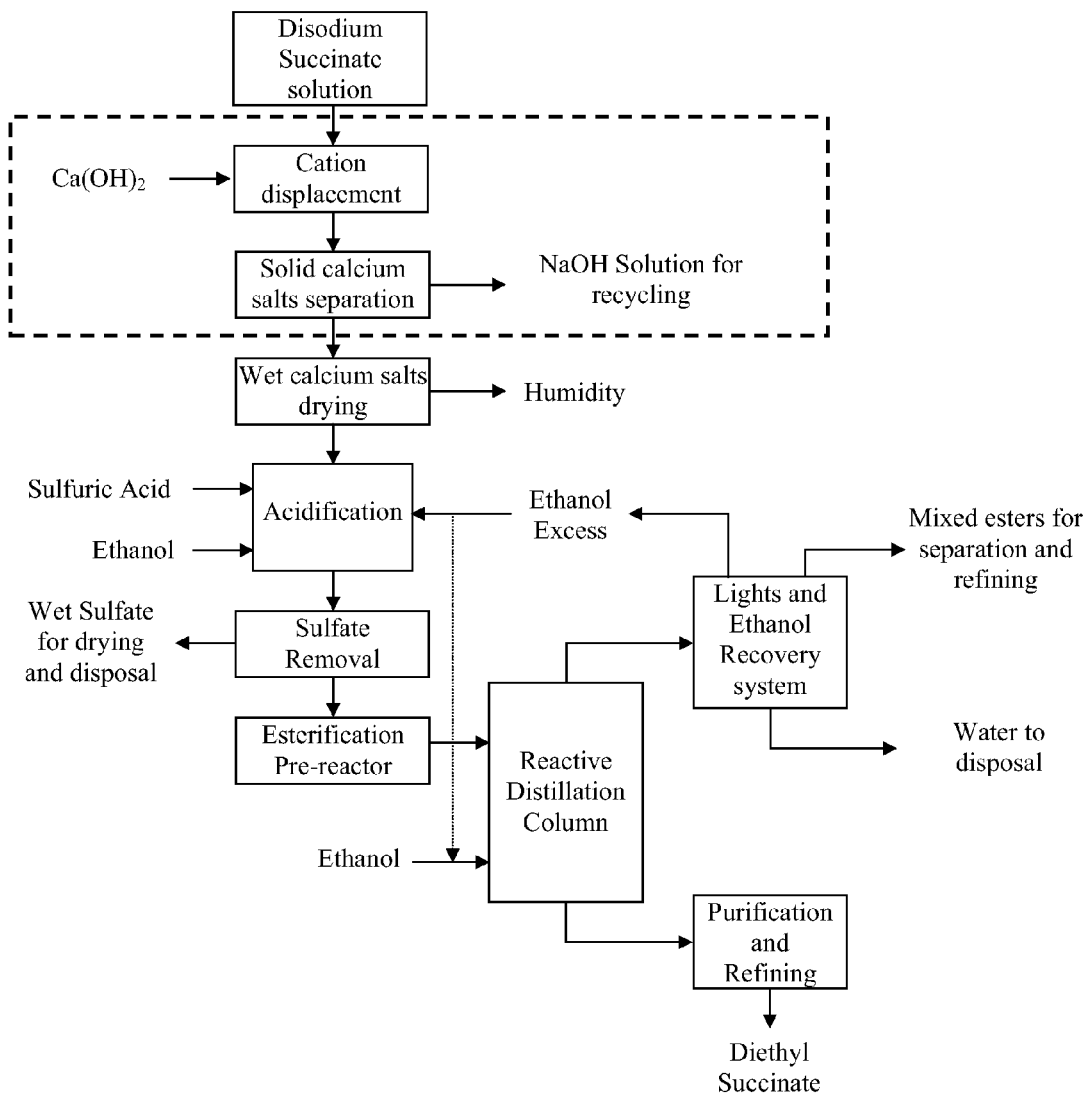
FIG. 3 illustrates a process flow diagram for succinic acid recovery from an aqueous solution, and its conversion to diethyl succinate using a reactive distillation process, including a Calcium-Sodium cation displacement method, according to embodiments of the invention.
Figure 4:
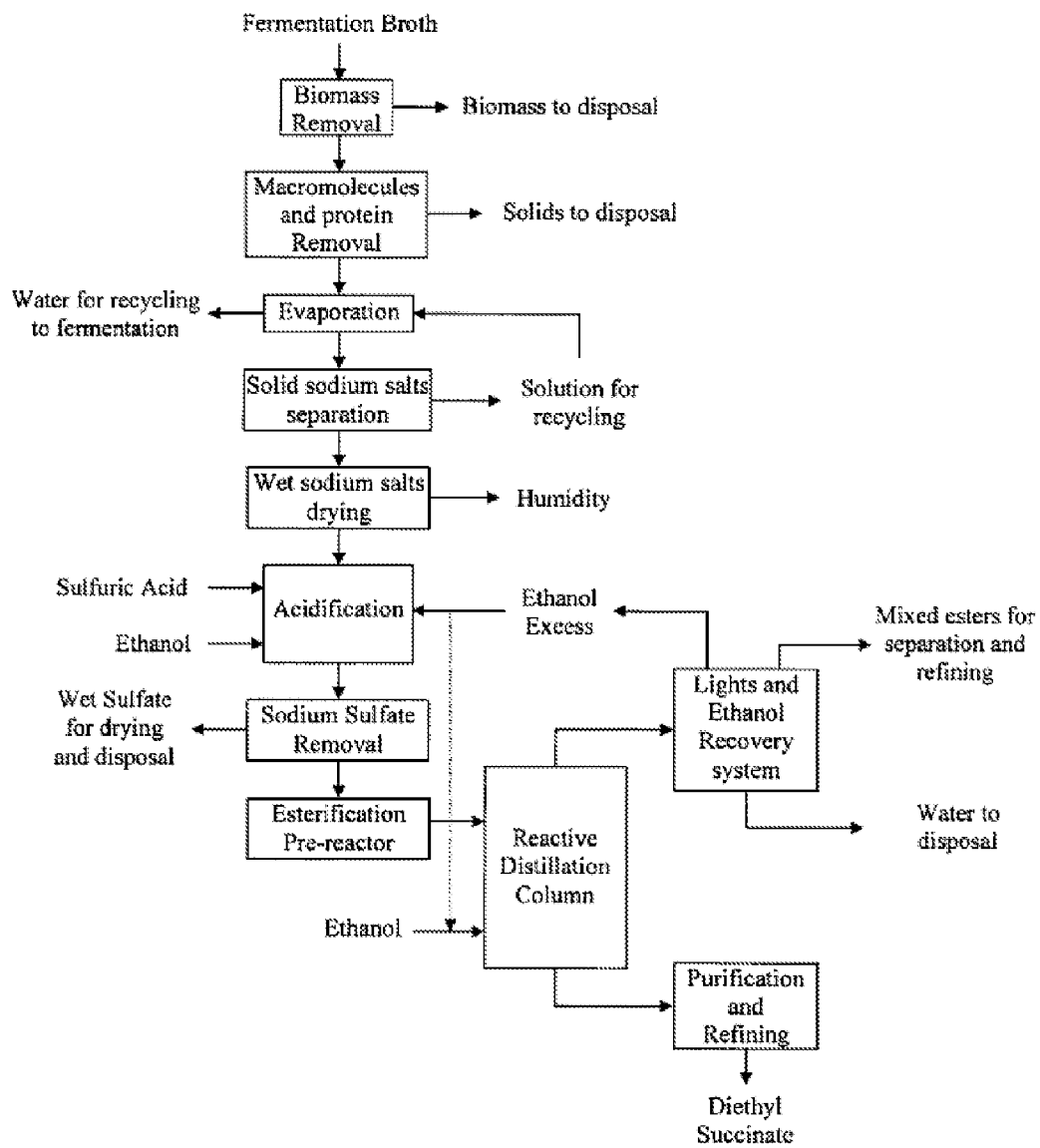
FIG. 4 illustrates a process flow diagram for an intermediate evaporation method that includes succinic acid recovery from fermentation broth and its conversion to diethyl succinate using a reactive distillation process, according to embodiments of the invention.
Figure 5:
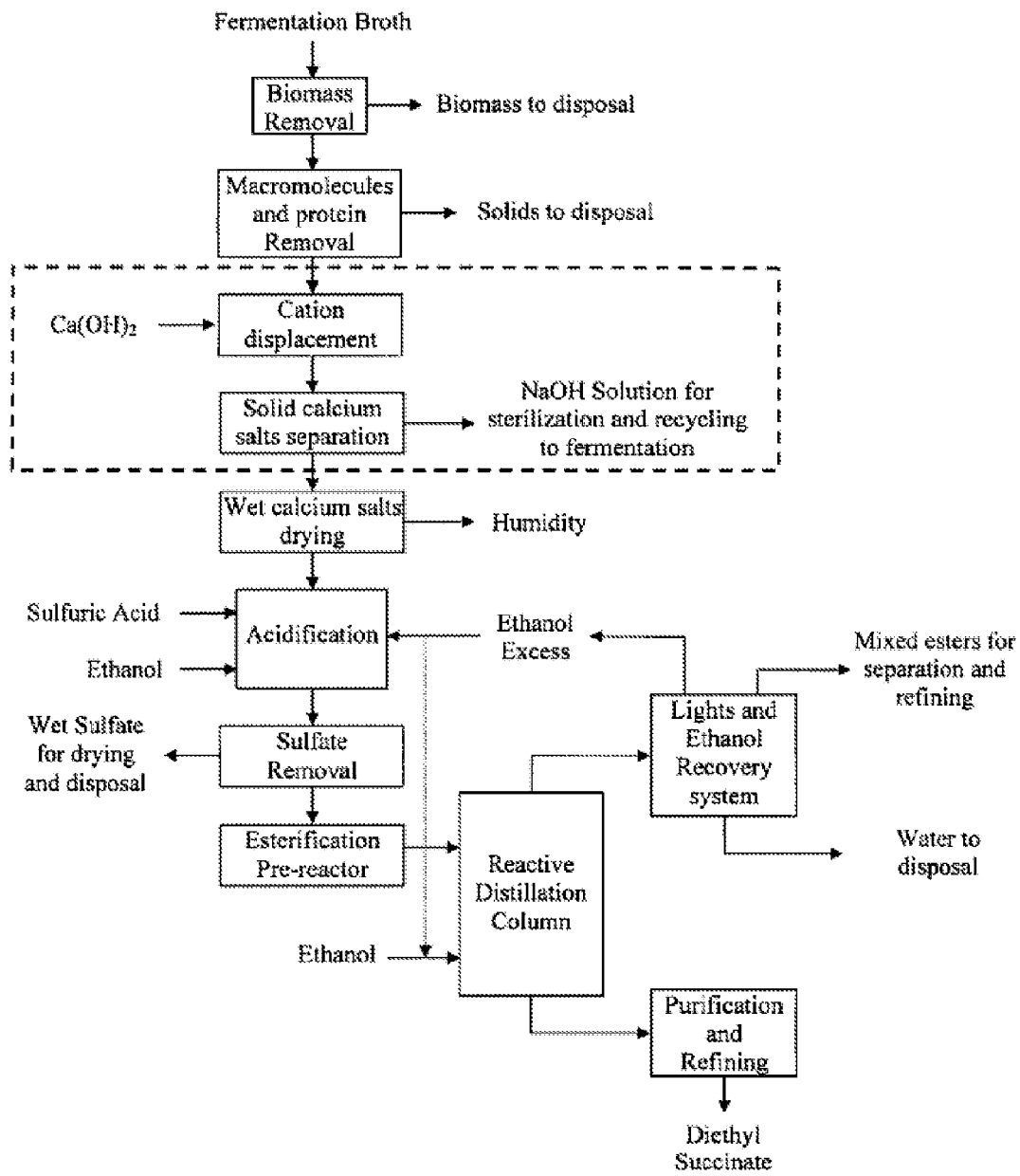
FIG. 5 illustrates a process flow diagram for a calcium-sodium cation displacement method that includes succinic acid recovery from fermentation broth and its conversion to diethyl succinate using a reactive distillation process, according to embodiments of the invention.

Representative process schemes for some embodiments are shown in FIGS. 2 and 3, for the recovery and purification of succinic acid esters from a disodium succinate solution, and in FIGS. 4 and 5, for the recovery and purification of succinic acid esters from fermentation broths.

FIG. 4 illustrates a flow diagram for the case in which sodium succinate is placed into ethanol and directly acidified by a mineral acid. FIG. 5 illustrates a flow diagram for the case in which the succinate is recovered by first precipitating calcium succinate via addition of calcium hydroxide, followed by separation of the calcium succinate, and then acidification with sulfuric acid to form calcium sulfate and succinic acid. FIGS. 4 and 5 illustrate similar processes that start from a fermentation broth. The process steps in the diagrams reflect both the steps taken in the purification at the laboratory scale as well as on a commercial scale.

Examples 1-3 provide the results of preliminary experiments to react sodium succinate with ethanol to form succinic acid. In Examples 1-3, the conversion of sodium succinate was estimated by drying the solids remaining in solution following reaction and then calcining them to determine the sodium content. This method gave reasonable estimations of extent and rate of reaction. The methods described in Examples 4-7 provide further refinements to these analytics.

Examples 4-7 describe experiments in which several identical reaction mixtures were prepared and simultaneously reacted for different lengths of time, thus providing a time profile of the acidification/esterification reaction. The analysis used in these experiments was significantly more precise than the calcination used in Examples 1-3, so the results are both more reliable and reproducible. As is seen in Tables 1-4, up to 98% of the sodium succinate initially present in ethanol was recovered in the alcohol solution as a free acid, monoethyl succinate, or diethyl succinate.

Example 8 describes experiments using the methods described in Example 4, but with only one tube per experiment used to obtain the final recovery of the carboxylic acids. Additional testing that can be carried out with variations of the methods described herein is discussed in Examples 9-12.

The invention will be further described by reference to the following examples, which are offered to further illustrate various embodiments of the present invention. It should be understood, however, that many variations and modifications may be made while remaining within the scope of the invention.

EXAMPLE 1

Model Extraction Procedure 1

A mixture of 10.02 g of 200 proof ethanol and 0.502 g of 98% sodium succinate was prepared and heated to 30° C. These quantities allowed for a final solution of 10 wt % succinic acid in ethanol to be obtained upon acidification. The solubility of succinic acid in ethanol at 30° C. is about 12 wt %. Sulfuric acid ($H_2SO_4$) (0.338 g, 98%) was added to the ethanol/sodium succinate slurry with stirring to produce free succinic acid and sodium sulfate.

After this acidification, the mixture was filtered using standard laboratory filtration methods (e.g., filter paper in a Buchner funnel). The filtered solution was collected in a receiving flask and the solid residue was rinsed with fresh ethanol until a neutral pH was obtained. The ethanol used for rinsing was then mixed with the filtered solution and ethanol was removed by drying under reduced pressure at 120° C. for 24 hours, until a constant weight was obtained.

The washed solid residue was then subjected to calcination in air in a muffle furnace at 700° C. for 24 hours, during which any sodium succinate present decomposed via the reaction:

$$C_4H_4O_4Na_{2(S)} + 7/2O_{2(g)} \rightarrow 4CO_{2(g)} + 2H_2O_{(g)} + Na_2O_{(S)}$$

Because sodium sulfate is stable under these conditions, the difference in weight between the initial dried solid residue and the final calcined solids gives the amount of sodium succinate remaining after the acidification step. Using this calculation, the conversion of sodium succinate into succinic acid was determined to be 60.5% after 2 hours, and 86% after 24 hours.

Analysis of the filtered ethanolic solution by gas chromatography (Hewlett Packard Model 5890) showed a low concentration of monoethyl succinate and diethyl succinate as products of esterification. Calculated conversion of succinic acid was approximately 1%, without addition of any catalyst. Higher conversions can be obtained with catalyst addition after filtration, as well as by using higher temperatures.

EXAMPLE 2

Model Extraction Procedure 2

Unless otherwise noted, all chemicals, equipment and procedures are as noted in Example 1.

A mixture of 31.83 g of 200 proof ethanol and 4.356 g of 98% sodium succinate was prepared and heated to 30° C. Sulfuric acid (2.817 g, 98%) was then added to the ethanol/sodium succinate slurry with stiffing to produce free succinic acid and sodium sulfate. Following the procedure described in Example 1, a conversion of 68.6% of sodium succinate was obtained after 1 hour.

EXAMPLE 3

Model Extraction Procedure 3

Unless otherwise noted, all chemical suppliers and equipment types are the same as in Example 1.

A mixture of 32.06 g of 200 proof ethanol and 4.325 g of 98% sodium succinate was prepared and heated to 30° C. $H_2SO_4$ (2.5386 g, 98%) was then added to the ethanol/sodium succinate slurry while stirring to produce free succinic acid and sodium sulfate. Following the procedure described in Example 1, a conversion of 86.6% of sodium succinate was obtained after 24 hours.

EXAMPLE 4

Because of challenges with both liquid and solid phases containing succinate species, and because water can be taken up and released in various forms, accurate results may be difficult to obtain under some conditions using the methods of Examples 1-3. Accordingly, a modified experimental procedure was adopted as described in this example to allow for accounting of the total recovery of succinic species in solid and liquid phases.

Experimental Procedures

A set of test tubes was loaded substantially identically with reagents, stirred at substantially identical rates, with the contents removed from reaction at different times. In each tube, the entire contents comprise the sample. Every reactor was stopped at different time intervals to mimic sampling in a batch reaction. In this experiment, the two phases were analyzed independently.

A solution of sulfuric acid in ethanol was prepared in a flask maintained in an ice bath to avoid heating and evaporation of the alcohol under mixing. Cappable 50 mL test tubes were charged with a defined amount of this solution (approx. 40 mL). Succinate salt was added to every tube at the stoichiometric amount to produce free succinic acid and sodium sulfate. The tubes were placed in a water bath (over a magnetic plate) at constant temperature, and mixed with magnetic stir bars. Each tube was taken out of the bath and quenched in ice at a different time in order to follow the kinetics of the reaction.

After centrifugation, of each tube at 6000 rpm for 15 minutes, the liquid layer was removed, weighed, and collected for analysis. The solids were washed in the same tube with anhydrous ethanol to remove any remaining soluble succinic species, and were centrifuged again to collect, weigh, and analyze the supernatant liquid. Finally, the solids were dissolved in water for further analysis. Because of the limited solubility of calcium sulfate in water, the solids were mixed with an aqueous solution of $H_2SO_4$ to dissolve any succinate remaining, and the liquid phase analyzed.

Following the experimental procedure described above, six test tubes were loaded with 4.13 g of sodium succinate hexahydrate ($Na_2C_4H_4O_4 \cdot 6H_2O$), 23.70 g of anhydrous ethanol ($C_2H_6O$), and 1.50 g of sulfuric acid ($H_2SO_4$). These quantities represent approximately the stoichiometric ratio for complete acidification to succinic acid and sodium sulfate. Those tubes were closed hermetically and placed simultaneously into the water bath at 30° C. One tube was removed from the bath at each of the following times of reaction: 15 min, 30 min, 1 h, 2 h, 3 h, and 6 h; and was processed for analysis. Molar recovery was calculated with respect to the total moles of succinic species initially loaded as the sodium salt. Mole percentages of succinic acid (SA), monoethyl succinate (MES), and diethyl succinate (DES) recovered in the liquid phase, are listed in Table 1.

TABLE 1

Acidification of $Na_2C_4H_4O_4 \cdot 6H_2O$
at 30° C. with Stoichiometric $H_2SO_4$

| Time | Succinate molar recovery in liquid phase mol % | | | | Succinate mol remaining in solid | Total succinic mol recovery |
|---|---|---|---|---|---|---|
| (h) | SA | MES | DES | TOTAL | phase Mol % | mol % |
| 0.25 | 33.72 | 20.26 | 3.77 | 57.75 | 43.72 | 101.46 |
| 0.5 | 60.68 | 14.57 | 1.07 | 76.33 | 22.02 | 98.34 |
| 1 | 42.05 | 21.26 | 4.5 | 67.80 | 32.59 | 100.39 |
| 2 | 82.68 | 7.78 | 0.43 | 90.89 | 10.44 | 101.33 |
| 3 | 78.09 | 12.31 | 0.91 | 91.30 | 13.67 | 104.97 |
| 6 | 62.97 | 14.17 | 0.9 | 78.05 | 14.11 | 92.15 |

EXAMPLE 5

The same experimental procedure described in Example 4 was followed. Each tube was loaded with 4.13 g of sodium succinate hexahydrate, 23.73 g of anhydrous ethanol, and 1.8 g of sulfuric acid, which corresponds to a 20% molar excess of $H_2SO_4$ relative to that required for acidification. Results of Example 2 are presented in Table 2.

TABLE 2

Acidification of $Na_2C_4H_4O_4 \cdot 6H_2O$
at 30° C. and 20% molar excess of $H_2SO_4$

| Time | Succinate molar recovery in liquid phase mol % | | | | Succinate mol remaining in solid | Total succinic mol recovery |
|---|---|---|---|---|---|---|
| (h) | SA | MES | DES | TOTAL | phase mol % | mol % |
| 0.25 | 57.03 | 24.73 | 3.29 | 85.06 | 19.91 | 104.97 |
| 0.5 | 48.17 | 27.3 | 4.3 | 79.785 | 13.62 | 93.41 |
| 1 | 57.33 | 27.13 | 2.73 | 87.2 | 2.01 | 89.22 |
| 2 | 48.21 | 38.36 | 3.62 | 90.2 | 1.55 | 91.75 |
| 3 | 39.31 | 47.51 | 11.92 | 98.75 | 1.23 | 99.99 |
| 6 | 31.43 | 50.68 | 14.23 | 96.35 | 1.36 | 97.72 |

EXAMPLE 6

The same experimental procedure described in Example 4 was followed. Each tube was loaded with 4.13 g of sodium succinate hexahydrate, 23.74 g of anhydrous ethanol, and 2.1 g of sulfuric acid, which corresponds to a 40% molar excess of $H_2SO_4$ relative to that required for acidification. Results of reaction are presented in Table 3.

TABLE 3

Acidification of $Na_2C_4H_4O_4 \cdot 6H_2O$
at 30° C. and 40% molar excess of $H_2SO_4$

| Time | Succinate molar recovery in liquid phase mol % | | | | Succinate mol remaining in solid | Total succinic mol recovery |
|---|---|---|---|---|---|---|
| (h) | SA | MES | DES | TOTAL | phase mol % | mol % |
| 0.25 | 14.1 | 27.53 | 11.18 | 52.83 | 52.87 | 105.7 |
| 0.5 | 49.77 | 31.90 | 4.1 | 85.78 | 6.88 | 92.66 |
| 1 | 10.04 | 16.30 | 8.41 | 34.75 | 61.78 | 96.54 |
| 2 | 43.73 | 29.54 | 6.16 | 79.44 | 2.39 | 81.83 |
| 3 | 27.35 | 48.25 | 14.18 | 89.79 | 1.17 | 90.96 |
| 6 | 4.79 | 40.93 | 47.26 | 92.99 | 0.43 | 93.43 |

EXAMPLE 7

Following the procedure described in Example 4, acidification of calcium succinate was evaluated. Each tube was loaded with 2.66 g of calcium succinate monohydrate ($CaC_4H_4O_4$), 23.77 g of anhydrous ethanol, and 1.49 g of sulfuric acid. These conditions correspond approximately to the stoichiometric amount of $H_2SO_4$ required for acidification to succinic acid and sodium sulfate. Results are presented in Table 4. Some scatter and loss of succinic acid can be attributed to small scale separation of solids from liquids during analysis, and to the limited solubility of calcium salts in water.

TABLE 4

Acidification of $CaC_4H_4O_4 \cdot 1H_2O$ at 30° C. with Stoichiometric $H_2SO_4$

| Time (h) | Succinate molar recovery in liquid phase mol % | | | | Succinate mol remaining in solid phase mol % | Total succinic mol recovery mol % |
|---|---|---|---|---|---|---|
| | SA | MES | DES | TOTAL | | |
| 0.25 | 4.91 | 15.98 | 32.2 | 53.09 | 27.26 | 80.35 |
| 0.5 | 4.52 | 12.98 | 29.47 | 46.97 | 34.46 | 81.43 |
| 1 | 13.95 | 25.95 | 15.67 | 55.59 | 24.39 | 79.98 |
| 2 | 29.83 | 35.47 | 10.28 | 75.59 | 12.41 | 88 |
| 3 | 29.7 | 39.64 | 23.37 | 92.72 | 7.62 | 100.35 |
| 6 | 29.55 | 29.07 | 10.71 | 69.34 | 8.15 | 77.5 |

EXAMPLE 8

Experiments were conducted using the methods described in Example 4, except that only one tube per experiment was used to obtain the final recovery of the carboxylic acids. The conditions and quantities of reagents used are given in Table 5. Results of the experiments are provided in Tables 6.

Because succinic acid and acetic acid are formed simultaneously by the microorganisms involved in a number of fermentations, mixtures of succinate salts and acetate salts were subjected to the experimental method described in Example 4 for the purpose of demonstrating the recovery of multiple acids simultaneously. Thus, a mixture of sodium acetate and disodium succinate hexahydrate (Run 5) was used as a model for the simultaneous recovery of succinic and acetic acid via the proposed process. Run 6 involved an azeotropic mixture of ethanol and water was used in place of anhydrous ethanol to recover succinic acid from aqueous solution. Runs 7 and 8 were conducted with sodium and calcium succinate salts at conditions that facilitate a high level of recovery of the succinic acid. Runs 1-4 were discarded due to procedural errors.

TABLE 5

Experimental conditions for acidification experiments

| Run | Time (h) | Salt | Succinic salt (g) | Acetic salt (g) | Ethanol (g) | $H_2SO_4$ (g) | T (C.) |
|---|---|---|---|---|---|---|---|
| 5 | 2 | $Na_2C_4H_4O_4 \cdot 6H_2O$ + $NaC_2H_3O_2$ | 2.42 | 0.15 | 20.42 | 1.16 | 50 |
| 6 | 2 | $Na_2C_4H_4O_4 \cdot 6H_2O$ | 2.43 | — | 20.21[‡] | 1.03 | 50 |
| 7 | 2 | $Na_2C_4H_4O_4 \cdot 6H_2O$ | 2.42 | — | 20.6 | 1.44 | 50 |
| 8 | 24 | $CaC_4H_4O_4 \cdot 1H_2O$ | 2.66 | — | 23.73 | 1.81 | 30 |

[‡]Ethanol 95% w/w

TABLE 6

Results of acidification under different conditions

| Run | Molar recovery in liquid phase mol % | | | | | Succinate mol remaining in solid phase mol % | Total succinic mol recovery mol % |
|---|---|---|---|---|---|---|---|
| | Acetic | | Succinic | | | | |
| | AcAc | EtAc | SA | MES | DES | | |
| 5 | 91.08 | 8.92 | 50.87 | 4.28 | 4.5 | 45.6 | 103.45 |
| 6 | — | — | 74.82 | 9.47 | 0.2 | 21.85 | 106.36 |
| 7 | — | — | 48.28 | 31.27 | 18.5 | 7.82 | 105.89 |
| 8 | — | — | 0.6 | 11.92 | 86.86 | 1.29 | 99.38 |

These experiments demonstrate the effectiveness of the novel methods described herein for recovering mixtures of organic acids simultaneously. These results also demonstrate that azeotropic mixtures of ethanol and water, which are much less expensive than anhydrous ethanol, are suitable as solvents for the recovery scheme. The results obtained expand the scope of conditions where the proposed recovery scheme is effective.

After demonstration of the process concept using pure succinate salts, a set of solids obtained from fermentation were subjected to the acidification/esterification process in EtOH. Characteristics of these solids are listed in Table 7.

EXAMPLE 9

Succinate Recovery from Fermentation Products

After demonstration of the process concept using pure succinate salts, a set of solids obtained from fermentation were subjected to the acidification/esterification process in EtOH. Characteristics of these solids are listed in Table 7.

TABLE 7

Characterization of culture broth solids

| Batch code | W-1 | 924-21b | 924-23 | 924-24 | 924-24m |
|---|---|---|---|---|---|
| Salt form | $Na^+$ | $Mg^{+2}$ | $Mg^{+2}$ | $Mg^{+2}$ | $H^+$ |
| Concentration wt % | | | | | |
| SA (wt %) | 24.8 | 38 | 39.6 | 38.4 | 52.6 |
| AcAc w % | 2.5 | — | — | — | — |
| Lactic acid | — | 5.2 | 5.5 | 5.8 | 0.87 |
| Other acids | — | ~3.0 | ~3.8 | ~3.8 | ~1 |
| Glucose w % | 29 | 0.4 | 0.36 | 0.42 | — |

Because of the high glucose content in sample labeled as W-1, a plastic-like sticky solid was obtained after drying.

Melting of glucose made difficult water removal under experimental conditions. For this reason, dispersion and dissolution of particles within the reactive media was difficult. Other solids were dried without major difficulties and particle size reduction was conducted until fine-brownish dusts were obtained. Solids from batch 924-24 m corresponded to crude SA obtained in the acid form because acidification was carried out in the aqueous broth before evaporation. In this case the amount of $H_2SO_4$ added was the required to catalyze esterification reaction (1 wt % of total solution).

Acidification conditions for fermentation solids are listed in Table 8 and results are summarized in Table 9. Experiments ("runs") 21 and 22 were carried out in 2 L batch reactors to evaluate the process in bench scale. In these runs reaction was performed under total reflux to avoid EtOH losses.

TABLE 8

Experimental conditions for acidification-esterification experiments on solids obtained from fermentation

| Run | Time (h) | Batch code | Solids (g) | EtOH (g) | $H_2SO_4$ (g) | Mole ratio $H_2SO_4$:SA | T (K) |
|---|---|---|---|---|---|---|---|
| 9 | 24 | W-1 | 5 | 19.8 | 1.3 | 1.1 | 303 |
| 10 | 6 | W-1 | 3 | 19.5 | 1.8 | 1.3 | 303 |
| 11 | 2 | W-1 | 3 | 19.7 | 0.9 | 1.3 | 323 |
| 12 | 8 | 924-21b | 2.04 | 6.7 | 0.7 | 1.04 | 303 |
| 13 | 5 | 924-21b | 2.01 | 7.4 | 0.9 | 1.43 | 303 |
| 14 | 5 | 924-21b | 2.01 | 7.4 | 0.9 | 1.44 | 333 |
| 15 | 8 | 924-23 | 2.04 | 6.7 | 0.7 | 0.98 | 303 |
| 16 | 5 | 924-23 | 2.03 | 7.8 | 1.0 | 1.4 | 303 |
| 17 | 5 | 924-23 | 2.02 | 7.7 | 1.0 | 1.41 | 333 |
| 18 | 8 | 924-24 | 2.03 | 6.8 | 0.8 | 0.98 | 303 |
| 19 | 5 | 924-24 | 1.99 | 8.3 | 1.0 | 1.57 | 303 |
| 20 | 5 | 924-24 | 2.01 | 8.3 | 1.0 | 1.57 | 333 |
| 21 | 24 | 924-24 | 399.8 | 1580 | 205 | 1.5 | 353 |
| 22 | 24 | 924-24m | 199.96 | 946.8 | 12.0 | 0.13 | 353 |

TABLE 9

Results of acidification-esterification of solids obtained from fermentation molar recovery of liquid phase

| | mol % | | | | | | |
|---|---|---|---|---|---|---|---|
| | Acetate | | | Succinate | | | |
| Run | AcAc | EtAc | TOTAL | SA | MES | DES | TOTAL |
| 9 | 53.1 | 38.1 | 91.2 | 61.7 | 15.1 | 0 | 76.8 |
| 10 | 15 | 31.6 | 46.6 | 7.3 | 14.6 | 12.6 | 34.5 |
| 11 | 20.6 | 36.7 | 57.3 | 20.0 | 22.8 | 9.4 | 52.2 |
| 12 | — | — | — | 43.2 | 10.2 | 6.2 | 59.8 |
| 13 | — | — | — | 58.4 | 8.6 | 1.3 | 68.3 |
| 14 | — | — | — | 73.4 | 5.2 | 3.9 | 82.6 |
| 15 | — | — | — | 46 | 2.9 | 3.7 | 52.6 |
| 16 | — | — | — | 57.1 | 18.6 | 3.4 | 79 |
| 17 | — | — | — | 61.2 | 2.4 | 3.2 | 66.8 |
| 18 | — | — | — | 51.8 | 6.1 | 4.4 | 62.4 |
| 19 | — | — | — | 57.3 | 9.3 | 1.3 | 67.9 |
| 20 | — | — | — | 78.8 | 6.1 | 5.2 | 90.1 |
| 21 | — | — | — | 13.6 | 54.1 | 33.3 | 101 |
| 22 | — | — | — | 1.3 | 12.1 | 73.4 | 86.9 |

Figure 6A:
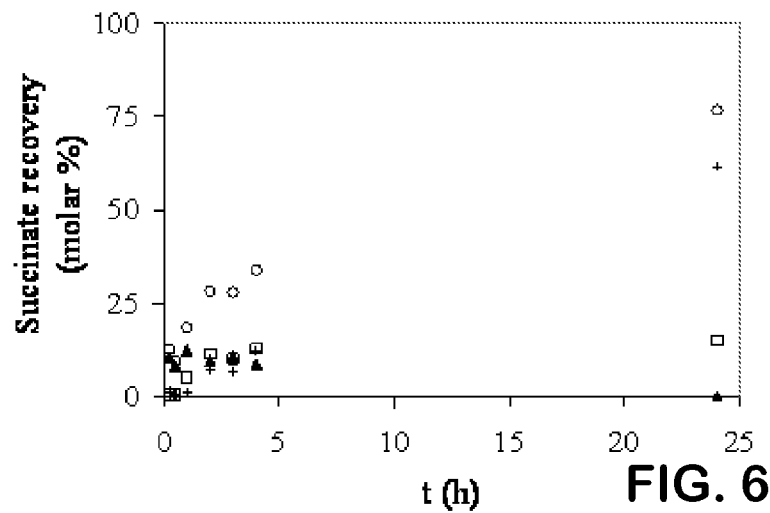
FIG. 6A shows recovery of succinate species in liquid phase over time during acidification of solids from fermentation broth, according to embodiments of the invention.
Figure 6B:
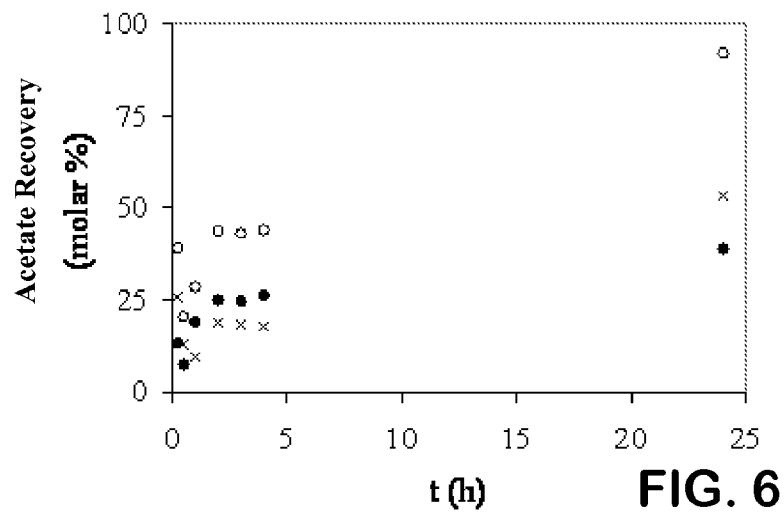
FIG. 6B shows recovery of acetate species in liquid phase over time during acidification of solids from fermentation broth, according to embodiments of the invention.

Even with excess of $H_2SO_4$, recovery of succinate and acetate species during acidification of solid W-1 was lower than that obtained with pure salts. After 2 h, around 40% recovery of succinate species was achieved compared with 80% in pure salts. However, after 24 h, comparable results with those obtained for pure solids are observed. This indicates that transport limitations are playing an important role in the process due to difficulties observed in dissolution of solids W-1. FIGS. 6A and 6B show the evolution of the recovery process in run 9 with FIG. 6A showing succinate species and FIG. 6B showing acetate species.

Recovery on Runs 12 to 22 was in general lower compared with pure salts. In these experiments sulfuric acid loading was calculated only with respect to SA, therefore when stoichiometric ratio was used molar loading was about 86% of the required to acidify all the acid species. This might explain the low recovery in experiments 12, 15 and 18. Remarkably, succinate esters were also produced during the process, confirming that $H_2SO_4$ acts as a catalyst before being consumed in salt acidification.

Figure 7A:
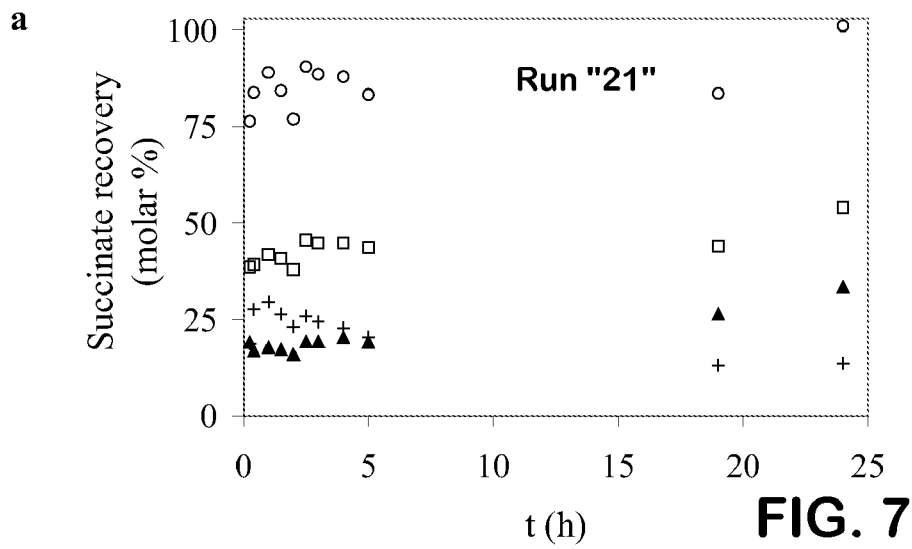
FIGS. 7A and 7B show recovery of succinate species in liquid phase over time during acidification of solids from fermentation in two different runs performed at bench scale, according to embodiments of the invention.
Figure 7B:
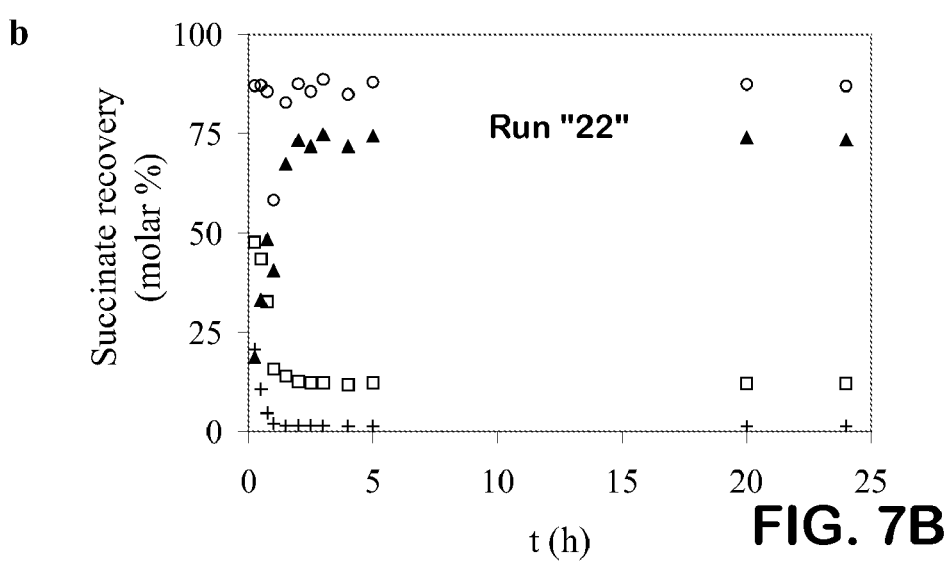

Increasing $H_2SO_4$ loading enhances recovery as observed in experiments 13, 16 and 19 but temperature is still low to promote esterification. Operating at higher temperatures (333 and 383 K) similar recoveries to those obtained with pure salts were achieved as noticed in runs 20 and 21. In bench scale experiments with succinate salts and with crude SA (runs 21 y 22) high recovery and high conversion to MES and DES were obtained verifying feasibility of the process in a big scale. Evolution of succinate recovery in bench scale experiments is presented FIGS. 7A and 7B.

EXAMPLE 10

Prophetic

Testing with other 'alcohol to organic acid' ratios will also be performed. For example, testing with a succinic acid to ethanol ratio ranging from greater than a six wt % equivalent succinic acid up to the stoichiometric amount of succinic acid to ethanol of 1:2 (required for formation of diethyl succinate) will be performed.

EXAMPLE 11

Prophetic

Alcohols other than ethanol will be tested as the solvent and esterifying agent, including, but not limited to, any $C_1$-$C_8$ alcohol.

EXAMPLE 12

Prophetic

Testing at temperatures higher than 25° C. up to the temperature where the alcohol (e.g., 78° C. for ethanol) or the organic acid start to decompose in the presence of sulfuric acid will also be performed.

EXAMPLE 13

Prophetic

Additional experiments directed to the use of concentrated aqueous solutions of succinate salts instead of solid salts will also be conducted. It is expected that the acid will still be recoverable, even with more water left in the solution.

EXAMPLE 14

Prophetic

Additional experiments directed at demonstrating the method with different organic acids will be conducted. Acids to be demonstrated can be, but are not limited to, maleic, oxalic, acetic, formic, lactic, citric, itaconic, 3-hydroxypropanoic, levulinic, fumaric, butyric, propionic, 2,5-furan dicarboxylic, aspartic, glucaric, glutamic, and pyruvic acids, and mixtures thereof.

Conclusions

The embodiments described herein provide methods for isolating a carboxylic acid, such as a dicarboxylic acid from its salt, as well as methods for esterifying a carboxylic acid. The carboxylic acids can be from a fermentation broth and the esterification can be carried out in a reactive distillation column.

As such, the methods described herein provide an improved method for the recovery and isolation of valuable co-product carboxylic acids as esters. The recovery of co-product acids also increases the efficiency of the feedstock conversion, otherwise affected by the loss of co-products to waste streams.

Unlike conventional methods which require isolation and purification of the carboxylic acid (e.g., succinic acid), the dissolution of acid salts into an alkanol solvent by addition of a mineral acid eliminates this requirement. As a result, energy and material consumption is reduced.

The novel methods further eliminate the need to use amines, solvents other than alkanols, ion exchange resins, and/or membranes. As a result, the separation steps are less complex, regeneration steps are not required and consumption of chemicals is decreased. Waste generation is also decreased, as compared to conventional methods. In one embodiment, only one mole of sulfate salts per mole of succinate is produced.

Additionally, evaporation and drying of acids in salt form, rather than free acid form, as is commonly performed in the art, significantly reduces losses of valuable compounds into the vapor phase, which also reduces the costs of waste treatment. Furthermore, the production of a pure water steam during evaporation steps, rather than an organic acid containing stream as is known in the art, can be used as an energy source and is also recyclable to the fermentor.

In traditional processes, acidification of the carboxylic acid salts in the aqueous phase with $H_2SO_4$ produces sulfate salts that are soluble in water. Those sulfates must be removed if pure succinic acid is desired. When esters are desired, solid catalysts can be poisoned or deactivated by the sulfate salts. Accordingly, removal of the sulfate salts is required in standard procedures. In the novel processes described herein, acidification in ethanol precipitates the sulfate salts, which are negligibly soluble in alkanols, and dissolves the free carboxylic acids, creating a solution ready for esterification. No separation from sulfate salts or purification of the free acids is required, and solid esterification catalysts can readily be used.

Partial dehydration of the alkanol/acids mixture can be achieved by formation of the sulfate salts, which are most stable in hydrated form (e.g. sodium sulfate decahydrate). Formation of the hydrated sulfate aids the removal of the hydration water of the original carboxylic acids salts (e.g., sodium succinate hexahydrate, sodium acetate trihydrate, calcium succinate monohydrate, calcium acetate monohydrate, and the like) and water produced during esterification, driving the reaction toward the ester products. Recovered alkanol from the process can also be used in this stage, thereby increasing the efficiency of the overall process.

Partial esterification can be achieved even in the acidification stage because of the large molar excess of ethanol with respect to carboxylic acids, and because $H_2SO_4$ can act as an esterification catalyst. Formation of esters in ethanol makes the solution more "organic" (e.g., hydrophobic) in nature, further reducing sulfate solubility and improving separation. The mixture of sulfate salts and the alkanol/carboxylic acid/ester can be readily filtered to remove sulfate salts. The organic acids and esters can then be sent to a reactive distillation chamber where the alkyl succinate can be separated and recovered from other esters.

All of the publications, including any and all articles, patents and published patent applications are incorporated by reference herein, each in their entirety, as though individually incorporated by reference. In the case of any inconsistencies, the present disclosure, including any definitions therein, will prevail.

Although specific embodiments have been illustrated and described herein, it will be appreciated by those of ordinary skill in the art that any procedure that is calculated to achieve the same purpose may be substituted for the specific embodiments shown. For example, although many of the embodiments discuss succinic acid, the novel methods described herein are useful for a broad range of carboxylic acids, such as those produced by fermentation, including, but not limited to maleic, oxalic, acetic, formic, lactic, citric, itaconic, 3-hydroxypropanoic, levulinic, fumaric, butyric, propionic, 2,5-furan dicarboxylic, aspartic, glucaric, glutamic, and pyruvic acids, and mixtures thereof. This disclosure is intended to cover any adaptations or variations of the present subject matter. Therefore, it is manifestly intended that embodiments of this invention be limited only by the claims and the equivalents thereof.

What is claimed is:

1. A method of producing an alkyl ester of a carboxylic acid comprising:
    adding an alkanol and a mineral acid to a carboxylic acid salt to provide a carboxylic acid/alkanol solution and a precipitated mineral acid salt;
    esterifying the carboxylic acid without separating the mineral acid salt from the carboxylic acid/alkanol solution; and
    isolating an alkyl ester of the carboxylic acid.

2. The method of claim 1 wherein the carboxylic acid comprises acetic acid, formic acid, lactic acid, acrylic acid, citric acid, 3-hydroxypropanoic acid, levulinic acid, propionic acid, butyric acid, isobutyric acid, pyruvic acid, 3- or 4-hydroxybutyric acid, succinic acid, malonic acid, maleic acid, malic acid, oxalic acid, itaconic acid, fumaric acid, 2,5-furan dicarboxylic acid, aspartic acid, glucaric acid, glutamic acid, adipic acid, pimelic acid, suberic acid, azeleic acid, sebacic acid, phthalic acid, isophthalic acid, terephthalic acid, or a combination thereof.

3. The method of claim 1 wherein the esterifying step is performed by heating the carboxylic acid/alkanol solution in a reactive distillation column, further wherein the carboxylic acid salt is an alkali metal salt, an alkaline earth metal salt, or a combination thereof, the mineral acid is sulfuric acid, the precipitated mineral acid salt is a sulfate salt, and the alkanol is a ($C_1$-$C_8$) alkanol comprising methanol, ethanol, propanol, butanol, pentanol, hexanol, heptanol, octanol, or a branched isomer of propanol, butanol, pentanol, hexanol, heptanol, or octanol.

4. The method of claim 3 wherein the propanol is n-propanol and the butanol is n-butanol, 2-butanol, or tert-butanol.

5. The method of claim 4 further comprising:
    adding additional alkanol to the reactive distillation column; and
    removing an alkanol-water azeotrope from the reactive distillation column, wherein the carboxylic acid salt is in an aqueous solution, and, prior to the adding step of claim 1, removing water from the aqueous solution to provide a carboxylic acid salt and water mixture containing less than about 15 wt % water.

6. The method of claim 5 wherein the carboxylic acid salt is a sodium salt and the method further comprises adding an alkaline earth metal hydroxide to the aqueous solution to exchange sodium cations of the carboxylic acid salt with alkaline earth metal cations.

7. The method of claim 6 wherein the aqueous solution of the carboxylic acid salt is part of an aqueous fermentation broth that includes water, bacteria, and nutrients, and the method further comprises:
removing organic solids from the aqueous fermentation broth to provide a separated fermentation broth that comprises the carboxylic acid salt;
removing water from the separated fermentation broth to precipitate the carboxylic acid salt or a carboxylic acid alkaline earth metal salt, to provide a carboxylic acid salt broth precipitate; and
adding an alkanol and a mineral acid to the carboxylic acid salt broth precipitate to provide a mixture of an alkanol solution of a resulting carboxylic acid and precipitated sodium sulfate or alkaline earth metal sulfate.

8. The method of claim 7 further comprising:
prior to the removing water step, removing organic compounds other than the carboxylic acid salt from the fermentation broth by treating the aqueous fermentation broth or the separated fermentation broth with an adsorption agent and adding an alkaline earth metal hydroxide to exchange sodium cations of the carboxylic acid salt with alkaline earth metal cations;
prior to the adding alkanol step, heating the carboxylic acid salt broth precipitate to remove additional water; and
concentrating the alkanol solution of the carboxylic acid to provide the carboxylic acid in concentrated form.

9. The method of claim 8 wherein the carboxylic acid salt comprises sodium succinate, the carboxylic acid comprises succinic acid, the mineral acid comprises sulfuric acid, and the alkyl ester of the carboxylic acid comprises diethyl succinate.

10. The method of claim 8 wherein the carboxylic acid comprises a monocarboxylic acid, a tricarboxylic acid, a tetracarboxylic acid, or a combination thereof, and the alkyl ester of the carboxylic acid comprises a monoalkyl ester, a dialkyl ester, a trialkyl ester, a tetraalkyl ester, or a combination thereof.

11. The method of claim 8 wherein the temperature of the alkanol/carboxylic acid solution and precipitated mineral acid sulfate or alkaline earth metal sulfate is about 23° C. to about the decomposition temperature of the alkanol or the organic diacid in the presence of aqueous sulfuric acid.

12. The method of claim 11 wherein the alkanol is ethanol and the temperature of the broth after adding the mineral acid is about 23° C. to about 78° C.

13. The method of claim 11 wherein the ratio of the amount of the carboxylic acid to alkanol in the alkanol/carboxylic acid solution and precipitated sodium sulfate or alkaline earth metal sulfate is about 5 wt % carboxylic acid in alkanol to about 1 molar equivalent of the carboxylic acid to 2 molar equivalents of alkanol.

14. The method of claim 13 wherein the ratio of carboxylic acid to alkanol is about 1 molar equivalent of the carboxylic acid to 2 molar equivalents of alkanol, and the corresponding dialkyl ester of the diacid is produced.

15. The method of claim 14 wherein the fermentation broth comprises an aqueous solution of a succinate salt, a solid form of a succinate salt, or both, further wherein sodium succinate is present in the fermentation broth.

16. The method of claim 14 wherein the carboxylic acid in the alkanol solution is converted to its corresponding alkyl diester, and the alkyl diester is isolated from other compounds by distillation to provide an isolated and purified alkyl diester.

17. The method of claim 16 wherein the carboxylic acid in the alkanol solution of the carboxylic acid is succinic acid, the isolated and purified alkyl diester is diethyl succinate and the mineral acid is sulfuric acid.

18. A method for isolating diethyl succinate comprising;
removing organic solids from an aqueous fermentation broth that includes water, bacteria, nutrients, and sodium succinate, to provide a separated fermentation broth that comprises sodium succinate;
optionally removing organic compounds other than the sodium succinate from the fermentation broth by treatment of the aqueous fermentation broth or the separated fermentation broth with activated carbon;
optionally adding an alkaline earth metal hydroxide to exchange sodium cations of sodium succinate with alkaline earth metal cations;
removing water from the separated fermentation broth to precipitate the sodium succinate or alkaline earth metal succinate, to provide a succinate broth precipitate;
optionally heating the succinate broth precipitate to remove additional water;
adding ethanol and sulfuric acid to the succinate broth precipitate to provide a mixture of an ethanol solution of succinic acid and precipitated sodium sulfate or alkaline earth metal sulfate;
esterifying the succinic acid in the ethanol solution in a reactive distillation column to provide diethyl succinate without separating the sodium sulfate or alkaline earth metal sulfate from the ethanol solution of succinic acid; and
isolating the diethyl succinate from other compounds in the reactive distillation column to provide isolated and purified diethyl succinate.

19. The method of claim 18 wherein the one or more of the other compounds in the reactive distillation column comprises succinic acid, malonic acid, maleic acid, malic acid, oxalic acid, itaconic acid, fumaric acid, 2,5-furan dicarboxylic acid, aspartic acid, glucaric acid, glutamic acid, adipic acid, pimelic acid, suberic acid, azeleic acid, sebacic acid, phthalic acid, isophthalic acid, terephthalic acid, acetic acid, formic acid, lactic acid, acrylic acid, citric acid, 3-hydroxypropanoic acid, levulinic acid, propionic acid, butyric acid, isobutyric acid, pyruvic acid, 3- or 4-hydroxybutyric acid, or their corresponding mono- or di($C_1$-$C_8$) alkyl esters, or a combination thereof.

20. The method of claim 19 wherein one or more of the corresponding alkyl esters of the carboxylic acid are isolated, further wherein prior to obtaining the separated fermentation broth, the fermentation broth is neutralized during fermentation to adjust the pH to biogenically acceptable levels.

21. The method of claim 20 wherein the pH range is adjusted to about 2 to about 10.

22. A method for making a commercial product comprising:
combining an alkanol and a mineral acid to a carboxylic acid salt to provide a carboxylic acid/alkanol solution and a precipitated mineral acid salt;
esterifying the carboxylic acid without separating the mineral acid salt from the carboxylic acid/alkanol solution;
isolating an alkyl ester of the carboxylic acid; and
further processing the alkyl ester to produce the commercial product.

* * * * *